United States Patent [19]

Milijasevic et al.

[11] Patent Number: 5,129,405
[45] Date of Patent: Jul. 14, 1992

[54] VEIN SUTURE COLLAR

[75] Inventors: Zoran Milijasevic, Elanora Heights; Sue Stewart, Paddington, both of Australia

[73] Assignee: Telectronics N.V., Netherlands

[21] Appl. No.: 559,407

[22] Filed: Jul. 26, 1990

Related U.S. Application Data

[63] Continuation of Ser. No. 339,894, Apr. 17, 1989, abandoned, which is a continuation of Ser. No. 113,350, Oct. 28, 1987, abandoned, which is a continuation of Ser. No. 776,859, Sep. 18, 1985, abandoned.

[51] Int. Cl.$^5$ ............................................. A61N 1/04
[52] U.S. Cl. .................................. 128/785; 128/786; 128/419 P
[58] Field of Search ............... 606/150, 152, 153, 155, 606/156; 128/784–786, 419 P; 623/1, 11, 12; 174/138 F

[56] References Cited

U.S. PATENT DOCUMENTS

| | | | |
|---|---|---|---|
| 3,113,997 | 12/1963 | Schneiderman | 174/138 F |
| 3,730,187 | 1/1973 | Reynolds | 604/174 |
| 4,437,475 | 3/1984 | White | 128/785 |
| 4,516,584 | 5/1985 | Garcia | 128/785 |
| 4,553,961 | 11/1985 | Pohndorf et al. | 604/175 |

FOREIGN PATENT DOCUMENTS

| | | |
|---|---|---|
| 2161708 | 1/1986 | United Kingdom . |
| 2090143 | 7/1987 | United Kingdom . |

OTHER PUBLICATIONS

Parsonnet et al.—J. Thorac. & Cardiovas. Surgery, #2, vol. 65, Feb. 1973 pp. 315–322.

*Primary Examiner*—C. Fred Rosenbaum
*Assistant Examiner*—William Lewis
*Attorney, Agent, or Firm*—Finnegan, Henderson Farabow, Garrett & Dunner

[57] ABSTRACT

A vein suture collar for anchoring an electrode lead to a vein in which the lead is inserted includes a sleeve member having three longitudinally spaced circumferential suture grooves in the exterior surface and a raised web area formed on the interior sleeve surface radially inward of each groove. The three raised web areas are angularly spaced about the sleeves axis and a longitudinal slit through the sleeve thickness can be provided. The slit collar can be separated at the slit and used to enclose the portion of the vein having the inserted electrode.

6 Claims, 2 Drawing Sheets

FIG. 1A
(PRIOR ART)
FIG. 1B
(PRIOR ART)
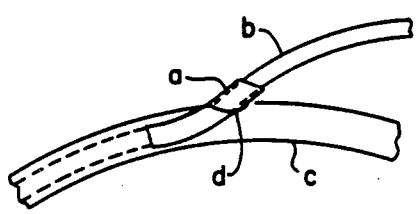
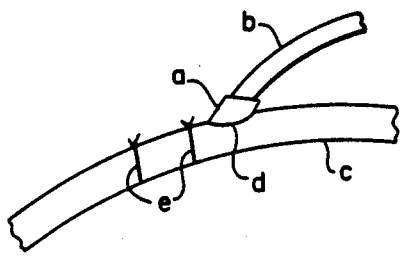
FIG. 2A
(PRIOR ART)
FIG. 2B
(PRIOR ART)
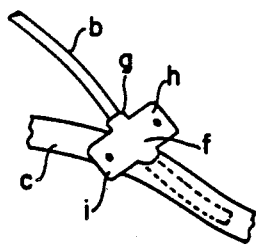
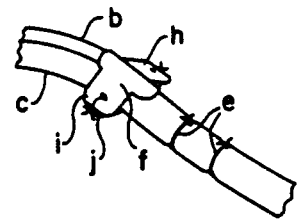
FIG. 3
(PRIOR ART)
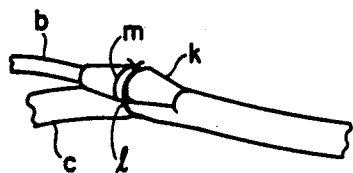

VEIN SUTURE COLLAR

This application is a continuation of application Ser. No. 07/339,894, filed Apr. 17, 1989, which is a continuation of application Ser. No. 113,350, filed Oct. 28, 1987, which is a continuation of application Ser. No. 06/776,859, filed Sep. 18, 1985, now abandoned.

BACKGROUND OF THE INVENTION

1. Field of the Invention:

The present invention relates to suture collars for use in ligating veins with inserted electrodes, to firmly tie the vein to the electrode, and a method of installation.

2. Description of the Prior Art:

It is well known that damage can occur to both polyurethane and silicone electrode leads if a suture is tightly tied around the body of the electrode lead. To avoid damage to the lead body, manufacturers have developed a variety of suture collars. There are three basic types of suture collars available on the market. The simplest, which is depicted in FIGS. 1A and 1B, is a silicone tube (depicted by the letter "a" in the Figures) which fits over electrode lead body "b" and is partially inserted into vein "c" at the lead entry site "d". Sutures "e" are then tied over the vein, sleeve and lead body. Although not shown, these collars generally have a longitudinal slit to facilitate installation over the lead body.

A slightly more sophisticated collar has a sleeve with a butterfly collar portion which can be anchored to the surrounding tissue. As depicted in FIGS. 2A and 2B, collar "f" includes butterfly portion "g" with wings "h", "i" which can be folded around vein "c" (FIG. 2B) and tied by suture "j".

The third type of collar is a sleeve with a groove formed in the collar exterior surface. As is depicted in FIG. 3, a collar "k" of this type sits on the vein and is anchored by tying suture "l" around groove "m" and vein "c".

Problems with conventional suture collars stem from the need to be able to slide the collar along the electrode lead into place at the vein entry site while still providing an anchor for the electrode lead. The bore of the collar typically is made only slightly larger than the outer diameter of the lead. However, small variations in either the collar inside diameter or the lead outside diameter can result in a situation where excessive interference is present and undue force is required to slide the collar, leading to possible damage to the lead, or a situation where the collar is too loose and no firm anchor is provided. Also, in either case the sutures can cut the vein if too much tension is applied, especially in the latter situation if the surgeon attempts to constrict the collar by tightening the sutures.

SUMMARY OF THE INVENTION

In accordance with the present invention, as embodied and broadly described herein, the vein suture collar comprises a cylindrical member having a through-bore along the longitudinal axis thereof, a plurality of circumferential grooves formed in the exterior surface of the member and spaced longitudinally, and a plurality of raised web areas formed on the interior surface of the member and extending radially into the through-bore.

Preferably, each of the plurality of raised web areas is located to radially oppose a respective one of the grooves.

It is also preferred that the raised web areas are angularly spaced about the interior surface of the member.

And it is still further preferred that the collar include a slit extending longitudinally along the entire length of the sleeve and radially through the thickness of the sleeve, and that the sleeve is resiliently spreadable at the slit to enclose the vein and the inserted electrode lead.

Further in accordance with the present invention, the method of installing a suture collar for use in tying a vein to an inserted electrode lead, the collar of the type comprising a cylindrical sleeve of a flexible material with a plurality of circumferential grooves in the exterior sleeve surface spaced in the longitudinal sleeve direction, comprises the steps of forming a slit in the sleeve in the longitudinal direction; separating the sleeve at the slit; enclosing the portion of the vein having the inserted electrode lead with the separated sleeve; and closing the sleeve at the slit. The closing step includes the step of applying sutures to each of the plurality of grooves to firmly abut the slit sleeve edges.

BRIEF DESCRIPTION OF THE DRAWINGS

FIGS. 1A and 1B are schematic representations of a conventional suture collar;

FIGS. 2A and 2B are schematic representations of another conventional suture collar;

FIG. 3 is a schematic representation of yet another conventional suture collar;

DESCRIPTION OF THE PREFERRED EMBODIMENT

Figure 4:
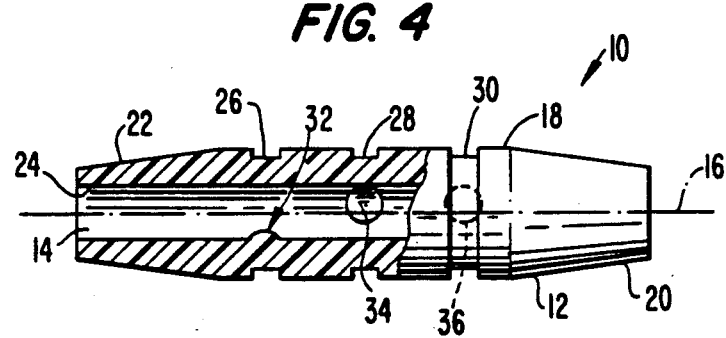
FIG. 4 is a schematic view in partial longitudinal cross section of a suture collar made in accordance with the present invention.
Figure 5:
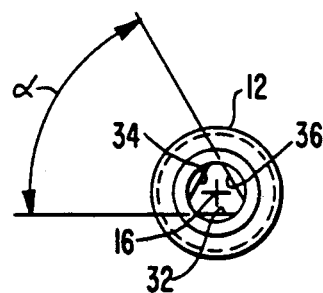
FIG. 5 is a schematic end view of the suture collar shown in FIG. 4.
Figure 6:
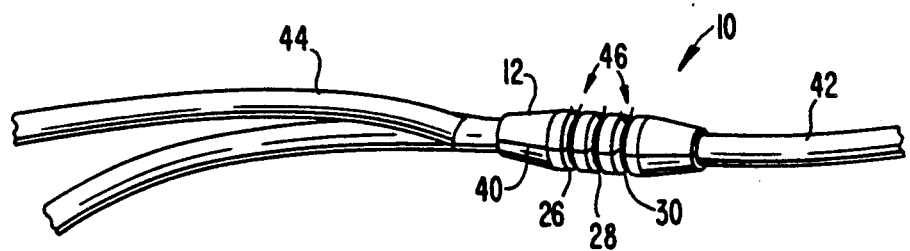
FIG. 6 shows a variant of the suture collar depicted in FIG. 4.

Reference will now be made in detail to the present preferred embodiment of the invention, an example of which is illustrated in FIGS. 4–6 of the accompanying drawings which show a suture collar designated generally by the numeral 10 made in accordance with the present invention. In accordance with the present invention, the vein suture collar comprises a cylindrical member having a through-bore along the longitudinal axis thereof. As embodied herein, and with initial reference to FIG. 4 of the drawings, suture collar 10 includes cylindrical sleeve 12 having through-bore 14 extending along longitudinal axis 16 of sleeve 12. Sleeve 12 can preferably be formed from medical grade silicone or any other flexible, bio-compatible low compression set material. Exterior cylindrical surface 18 of member 12 is tapered at opposing longitudinal ends. In the embodiment shown in FIG. 4, interior cylindrical surface 24 of sleeve 12 has a generally constant diameter along longitudinal axis 16, except for the raised web areas to be discussed hereinafter. The I.D. of the collar generally varies from about 0.25 mm to about 0.35 mm larger than the O.D. of the electrode lead, the variation depending upon the stiffness of the lead, insulation material surrounding the lead (polyurethane or silicone) and whether the lead is unipolar or multipolar.

Further in accordance with the present invention, the vein suture collar further comprises a plurality of circumferential grooves formed in the exterior surface of the member and spaced longitudinally. As embodied herein, and with continued reference to FIG. 4, a total of three circumferential grooves 26, 28, 30 are formed in exterior surface 18 and spaced along longitudinal axis 16. Grooves 26, 28, 30 should be sized to accommodate and capture the suture thread to be used to ligate the vein.

Still further in accordance with the present invention, the vein suture collar includes a plurality of raised web areas formed on the interior surface of the cylindrical member and extending radially into the through-bore. As embodied herein, and with reference to FIGS. 4 and 5, a total of three raised web areas 32, 34, 36 are formed on interior surface 24 and extend radially into through-bore 14. It is intended that raised web areas 32, 34, 36 provide the primary contact between collar 10 and the inserted electrode. Thus, for applications where collar 10 is to be used in the manner of conventional suture collars where direct contact between the electrode lead and the collar occurs, the interior diameter 24 of sleeve 12 can be made larger than the outside diameter of the electrode lead by a margin sufficient to preclude interference between the interior surface 24 and the electrode lead. Concurrently, raised web areas 32, 34, 36 should be sized to provide an interference fit with electrode lead to a degree only to inhibit movement of the collar by gravity alone, while permitting collar 10 to be manually slid along the electrode lead with a small force. The lead-contacting surfaces of raised web areas 32, 34, 36 should be smooth and can preferably be made circular and rounded as depicted in the figures. However, other web area shapes can be used.

Preferably, the web areas are spaced longitudinally along the axis of the cylindrical member and are formed radially beneath respective circumferential suture grooves. As embodied herein, and with reference to FIGS. 4 and 5, raised web areas 32, 34, 36 are formed at the same longitudinal locations and radially inward of grooves 26, 28, 30, respectively. This correspondence permits the force exerted by the sutures to be radially directed through the web areas 32, 34, 36 to the electrode lead and permit collar 10 to be flexed between these longitudinal locations.

It is also preferred that raised web areas be angularly distributed on the interior surface about the cylindrical member longitudinal axis. As embodied herein, and with reference to FIG. 5, the three web areas of the preferred embodiment are angularly displaced at about 60 degree intervals as shown by the angle designated alpha. Relative to axis 16, the angular spacing of the three raised web areas would be 120°, as will be appreciated from FIG. 5. This angular distribution acts to force a plurality of contacts between the lead and the interior surface 24 of collar 10.

In accordance with the present invention, vein suture collar further comprises a slit extending longitudinally along the entire length of the sleeve and radially through the thickness of the sleeve. As a result of the flexible sleeve material, the sleeve can be resiliently spread at the slit to enclose both the vein and inserted electrode lead in a preferred installation mode. As embodied herein and as depicted in FIG. 6, collar 10 can include slit 40 in cylindrical sleeve 12 along the longitudinal direction and through the thickness of sleeve 12. Slit 40 permits collar 10 to be used to protect both the vein (designated 42 in FIG. 6) and the electrode lead (designated 44) from being damaged by tightening of sutures 46 in grooves 26, 28 30. Collar 10 with slit 40 can thus be used in a manner different from conventional suture collars.

Specifically, and in accordance with the preferred installation method of the present invention, installation of the collar is accomplished by separating the flexible collar at the slit and enclosing the vein and inserted lead with the separated collar. Following the enclosing step, the sutures are tied around the circumferential grooves to cause the slit edges of cylindrical sleeve to firmly abut. For applications using a slit collar, the raised web areas can be formed to provide a lesser degree of interference with the electrode lead inasmuch as the raised web areas will not contact the electrode lead directly but through the thickness of the vein wall.

It will be apparent to those skilled in the art that various modifications and variations can be made in the vein suture collar of the present invention without departing from the scope or the spirit of the invention. It is intended that the present invention cover the modifications and variations of this invention provided they come within the scope of the appended claims and their equivalents.

What is claimed is:

1. A vein suture collar for anchoring an electrode lead in a vein into which the lead is inserted, comprising:
   a flexible cylindrical member having a through-bore along the longitudinal axis thereof, the through-bore having an internal diameter larger than the outside diameter of the electrode lead to be inserted therein;
   a plurality of circumferential suture grooves formed in the exterior surface of said member and spaced longitudinal relative to the axis; and
   engaging means, comprising a plurality of spaced raised web areas formed on the interior surface of the through-bore integrally with said member and extending radially into said through-bore, for frictionally engaging the electrode lead upon insertion of the lead into the through-bore even absent any sutures being tied about said circumferential grooves and without deforming the electrode lead, said raised web areas being spaced from each other along the longitudinal aixs of said member and being substantially equi-angularly spaced relative to each other about the interior surface of said member, said raised web areas adapted for gripping the electrode lead and the vein at predetermined longitudinal positions when sutures are tied about said circumferential grooves and without restricting the overall circumference of the vein at any single longitudinal location.

2. The collar as recited in claim 1, wherein each of said raised web areas has a generally circular surface area for contacting the electrode lead upon insertion of the lead into the through-bore.

3. The collar as recited in claim 1, wherein each of said raised web areas is located to radially oppose a respective one of said grooves.

4. The collar as recited in claim 3, wherein said plurality of grooves comprises three grooves.

5. The collar as recited in claim 1, further comprising a slit extending longitudinally along the entire length of said member and radially therethrough, the member being resiliently spreadable at said slit to enclose the vein and electrode lead inserted therein.

6. A vein suture collar for anchoring an electrode lead in a vein into which the lead is inserted, comprising:
   a flexible cylindrical member having a through-bore having an internal diameter larger than the outside diameter of the electrode lead to be inserted therein;

three circumferential suture grooves formed in the exterior surface of said member and spaced longitudinal relative to the axis; and engaging means, comprising three spaced raised web areas formed on the interior surface of the through-bore integrally with said member and extending radially into said through-bore, for frictionally engaging the electrode lead upon insertion of the lead into the through-bore even absent any sutures being tied about said circumferential grooves and without deforming the electrode lead, said raised web areas being spaced from each other along the longitudinal axis of said member, being angularly spaced relative to each other about the interior surface of said member at about 120° intervals with respect to the axis, and being individually disposed radially opposite respective ones of said grooves, said raised web areas adapted for gripping the electrode lead and the vein at predetermined longitudinal positions when sutures are tied about said circumferential grooves and without restricting the overall circumference of the vein at any single longitudinal location.

* * * * *